(12) United States Patent
Kenneally et al.

(10) Patent No.: US 6,455,716 B2
(45) Date of Patent: Sep. 24, 2002

(54) PROCESS FOR THE BRANCHING OF SATURATED AND/OR UNSATURATED FATTY ACIDS AND/OR ALKYL ESTERS THEREOF

(75) Inventors: Corey James Kenneally, Mason, OH (US); Daniel Stedman Connor, Cincinnati, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 68 days.

(21) Appl. No.: 09/798,600

(22) Filed: Mar. 2, 2001

Related U.S. Application Data

(60) Provisional application No. 60/186,924, filed on Mar. 3, 2000.

(51) Int. Cl.$^7$ .............................................. C07C 51/00
(52) U.S. Cl. ....................... 554/158; 554/128; 554/141; 554/145; 502/77; 502/78
(58) Field of Search ................. 554/158, 125, 554/141, 145; 502/77, 78

(56) References Cited

U.S. PATENT DOCUMENTS

| | | | |
|---|---|---|---|
| 3,090,807 A | | 5/1963 | Illing et al. |
| 4,430,252 A | | 2/1984 | Ryu |
| 4,560,790 A | | 12/1985 | Ryu |
| 4,882,307 A | | 11/1989 | Tsao |
| 4,943,546 A | | 7/1990 | Travers et al. |
| 4,973,431 A | | 11/1990 | Struve et al. |
| 5,306,855 A | | 4/1994 | Periana et al. |
| 5,364,949 A | | 11/1994 | Neuss et al. |
| 5,525,126 A | | 6/1996 | Basu et al. |
| 5,677,473 A | * | 10/1997 | Tomifuji et al. ............ 554/158 |
| 5,840,942 A | | 11/1998 | Oude Alink |
| 5,856,539 A | | 1/1999 | Hodgson et al. |

FOREIGN PATENT DOCUMENTS

WO   WO 98/07680 A1   2/1998

OTHER PUBLICATIONS

Ullman's Encyclopedia of Industrial Chemistry, A5 (5$^{th}$ Ed.), p. 239–240. 1986. *Saturated Monocarboxylic Acids and Unsatured Monocarboxylic Acids*.

* cited by examiner

*Primary Examiner*—Deborah Carr
(74) *Attorney, Agent, or Firm*—Armina E. Matthews; Kim William Zerby; Steven W. Miller

(57) ABSTRACT

A process for the branching of saturated and/or unsaturated fatty acids and/or alkyl esters thereof comprises subjecting the fatty acids and/or alkyl esters to a skeletal isomerization reaction using a catalyst comprising a crystalline porous structure having incorporated therein a metal to form metal sites on said catalyst and isolating branched fatty acids, alkyl esters thereof, or mixtures thereof, from a reaction mixture obtained by said skeletal isomerization reaction. The catalyst used in the isomerization reaction is preferably a zeolite catalyst containing metal sites of a Group VIII metal. The process produces a mixture of fatty acids and/or alkyl esters that contain significant quantities of branched molecules.

18 Claims, No Drawings

PROCESS FOR THE BRANCHING OF SATURATED AND/OR UNSATURATED FATTY ACIDS AND/OR ALKYL ESTERS THEREOF

CROSS REFERENCE TO RELATED APPLICATION

This application claims the benefit of U.S. Provisional Application No. 60/186,924, filed Mar. 3, 2000.

TECHNICAL FIELD

The present invention relates to a process for the branching of saturated and/or unsaturated linear fatty acids and/or alkyl esters thereof utilizing a crystalline, porous solid acid catalyst, such as a zeolite, which also contains metal sites.

BACKGROUND OF THE INVENTION

Branched alkyl fatty acids and alkyl esters are useful in a number of consumer products, including surfactants, fabric conditioners, cosmetics, and lubricants. Branched fatty acids and alkyl esters which are saturated offer a number useful features, including lubricity/surfactancy due to their chain-length and random branching, oxidative stability due to little or no carbon—carbon double bonds present, and low crystallinity over a wide range of temperatures due to a significantly lower melt point compared to their linear counterparts.

A number of various processes for making branched fatty acids and esters have been previously disclosed. One approach involves the exclusive use of unsaturated fatty acids or alkyl ester feedstocks using a microporous catalyst. For example, U.S. Pat. No. 5,856,539, issued Jan. 5, 1999 to Hodgson et al., discloses a process for converting unsaturated fatty acids into branched fatty acids by using catalysts having a microporous. structure, such as zeolites. In addition, U.S. Pat. No. 5,677,473, issued Oct. 14, 1997 to Tomifuji et al., discloses a process for preparing branched chain fatty acids or alkyl esters by subjecting unsaturated fatty acids or esters having 10 to 25 carbon atoms to a skeletal isomerization reaction in the presence of water or a lower alcohol using a zeolite catalyst having a linear pore structure that is small enough to minimize dimerization and large enough to allow diffusion of the branched molecules. Both of these patents have numerous disadvantages, including high feedstock costs (i.e. oleic acid), relatively high yields of by-products such as oligomers, and high equipment capital costs due to the need for custom separation processes (i.e. molecular distillation to recover dimers and trimers).

A second approach involves the use of saturated fatty acids and non-microporous catalysts. For example, U.S. Pat. No. 3,090,807, issued May 21, 1963 to Illing, describes the branching of saturated aliphatic carboxylic acids by heating with carbon monoxide in the presence of (a) a metal carbonyl, (b) a halogen, such as chlorine, bromine, or iodine, (c) an activator, such as compounds of bismuth, antimony, titanium, boron, iron, or tin, and (d) water. In addition, WO 98/07680 published Feb. 26, 1998 by Roberts et al., describes the branching of saturated or unsaturated fatty acids or their derivitives using a binary ionic liquid catalyst, such as a metal chloride and/or an organic or inorganic halide salt. Both of these patents have numerous disadvantages, including high operating costs associated with using the types of catalysts described above, high equipment capital costs associated with corrosion prevention when using halogens or ionic liquids, and also the environmental issues associated with disposal of these materials.

A third approach is a totally synthetic based route to making branched fatty acids or alkyl esters. Ullman's Encyclopedia of Industrial Chemistry (Volume A5, $5^{th}$ Ed., 1986, pp. 239–240) describes four different approaches to making synthetic fatty acids, including carbonylation of olefins, carboxylation of olefins, oxidation of alkanes, and alkali fusion of alcohols. The first two approaches result in significant quantities of branched molecules. Carbonylation of olefins is currently the principal method for the commercial production of $C_4$–$C_{13}$ carboxylic acids. Because of the complex nature of the olefinic raw materials, the higher carboxylic acids obtained in this process ($C_8$ and higher) are usually mixtures of branched chain products. The disadvantages of these types of approaches to making branched acids and/or alkyl esters include the high capital cost and yield losses associated with a multi-step synthetic route (i.e. linear olefin synthesis, olefin branching, hyroformulation, and oxidation for the carbonylation process) vs. that of the natural route (i.e. hydrolysis of triglycerides, followed by branching of the fatty acid), as well as the undesirability of using non-renewable, petroleum based feedstocks as opposed to using renewable, natural based fatty acid or methyl ester feedstocks.

Crystalline, microporous solid acid catalysts, containing metal sites have also been disclosed. For example, U.S. Pat. No. 4,882,307, issued Nov. 21, 1989 to Tsao discloses a process for preparing noble metal-containing zeolites having high metal dispersion. The catalysts are used in processes such as hydrogenation, dehydrogenation, dehydrocyclization, isomerization, hydrocracking, dewaxing, and reforming of materials such as hydrocarbons. However, these types of catalysts have not heretofor been used to catalyze isomerization reactions to branch saturated and/or unsaturated fatty acids and/or alkyl esters thereof.

It is the object of the present invention to create an efficient process for branching saturated or unsaturated fatty acids and/or alkyl esters thereof to achieve significant quantities of branched molecules using a crystalline, microporous solid acid catalyst, such as a zeolite, with metal sites present.

It is a further object of the present invention to create a process that uses renewable, natural-based feedstocks such as linear fatty acids derived from vegetable or animal sources, which is also environmentally friendly from the standpoint of waste disposal of catalysts or other process aids.

SUMMARY OF THE INVENTION

The present invention encompasses a process for branching saturated and/or unsaturated fatty acids and/or alkyl esters thereof comprising the steps of:

(a) subjecting a feedstock comprising saturated and/or unsaturated fatty acids having from 3 to 25 carbon atoms, alkyl esters thereof, or mixtures thereof, to a skeletal isomerization reaction using a catalyst comprising a crystalline porous structure having incorporated therein a metal to form metal sites on said catalyst; and (b) isolating branched fatty acids, alkyl esters thereof, or mixtures thereof, from a reaction mixture obtained by said skeletal isomerization reaction.

The catalyst utilized in the present process is preferably a zeolite catalyst containing metal sites of Group VIII metal. The process is carried out in the presence of hydrogen gas, or a mixture of gases including hydrogen gas, under pressure.

The present invention further encompasses the present process further comprising a recycle step in which higher yields of branched molecules can be obtained.

DETAILED DESCRIPTION OF THE INVENTION

It has now been found that it is possible to convert (by isomerization) a feed of fatty acids and/or alkyl esters comprising saturated and/or unsaturated fatty acids and/or alkyl esters thereof (e.g. oleic, stearic, palmitic, myristic) into a mixture which has a significant content of branched fatty acids and/or alkyl esters. In the present process, a fatty acid and/or alkyl ester feed comprising either saturated and/or unsaturated fatty acids and/or alkyl esters is contacted with a catalyst, wherein the catalyst comprises a material having a crystalline microporous structure containing metal sites, preferably a zeolite catalyst containing metal sites, particularly Group VIII metal sites. The reaction which is the subject of this invention can be seen as an isomerization reaction (involving both skeletal and positional isomerization). The branching reaction is herein included.

The process of the present invention is to prepare branched chain fatty acids and/or alkyl esters thereof from either saturated and/or unsaturated fatty acids and/or alkyl esters having a total carbon number of from about 3 to about 25, comprising at least a step wherein skeletal isomerization is carried out at a temperature of from about 240° C. to 380° C., preferably in the presence of a gas selected from the group consisting of hydrogen, nitrogen, carbon dioxide, argon, and mixtures thereof, using a zeolite catalyst having a linear pore structure with a pore size small enough to retard oligomerization and aromatization, and large enough to allow diffusion of branched chain saturated fatty acids and/or alkyl esters thereof.

When a starting material mixture contains both fatty acids and alkyl esters thereof, both branched chain fatty acids and alkyl esters thereof can be produced, because both can be isomerized simultaneously. Such cases are also included in the technical scope of the present invention.

The saturated and/or unsaturated fatty acid and/or alkyl ester used as the starting material are fatty acids and/or alkyl esters having a total carbon number of from about 3 to 25, preferably from about 10 to about 25, and more preferably from about 12 to about 24. Considering industrial applications, it is further preferable that a major component of the starting material has a total carbon number of about 18, such as stearic acid. Branched fatty acids having a total carbon number of this range are useful as starting materials for the synthesis of fabric conditioners, cosmetic bases, lubricating oil additives, and the like.

In the processes of the present invention, the starting material can be a saturated and/or unsaturated fatty acid and/or alkyl ester, and mixtures thereof. In a preferred process wherein the reaction is carried out in the presence of hydrogen gas, or a mixture of gases including hydrogen gas, any unsaturated molecules present tend to be quickly hydrogenated into saturated fatty acids and/or alkyl esters in the process described. It is preferable that the content of the unsaturated molecules in the starting material be kept below 50%, more preferably below 10%, most preferably below 1%, in order to minimize formation of by-products such as oligomers in the process. In a preferred embodiment, the starting material (i.e. the feedstock) in the present process comprises saturated fatty acids and/or alkyl esters and is essentially free of unsaturated fatty acids and/or alkyl esters. Catalytic hydrogenation can also be used to convert all or some of the unsaturated molecules present in the feedstock into the corresponding saturated molecules prior to using the branching process described herein.

Suitable fatty acids include oleic acid, stearic acid, palmitic acid, and myristic acid, which can be produced by hydrolysis of triglycerides of vegetable or animal origin, including beef tallow, palm oil, palm kernal oil, coconut oil, tall oil, canola oil, and soybean oil. Synthetic fatty acids produced from petrochemical feedstocks which are substantially linear can also be used. The starting material can be a mixture containing one or more of these saturated or unsaturated fatty acids, or alkyl esters thereof.

From the viewpoint of minimizing cost of the branched fatty acids and/or alkyl esters, it is preferable that the above-described starting material be derived from low cost feedstocks such as tallow or soybean oil, which are typically rich in stearic and palmitic acids.

Alkyl esters of saturated and/or unsaturated fatty acids having a total carbon number of from about 3 to about 25, preferably from about 10 to about 25, and more preferably from about 12 to about 24, used as a starting material are those corresponding to the above-described saturated fatty acids. That is, alkyl esters of the saturated and/or unsaturated fatty acids exemplified above can be used. Although the alkyl moiety is not subject to limitation as to carbon number, its carbon number is normally 1 to 4, preferably 1. Specific examples of alkyl esters include methyl esters, ethyl esters and propyl esters of the above-mentioned saturated and/or unsaturated fatty acids, with preference given to methyl esters.

Catalysts used in the processes of the present invention are generally crystalline porous structures containing metal sites. Suitable crystalline porous structures useful in the present processes include both mesoporous and microporous structures. As used herein, the term "mesoporous" refers to structures containing pores having diameters of from about 10 to about 100 angstroms, and the term "microporous" refers to structures containing pores having diameters of less than about 10 angstroms. Preferably, the catalyst has a crystalline microporous structure. The catalysts herein typically have an acidic crystalline porous structure.

Crystalline microporous structures generally encompass two broad classes of materials, zeolites and non-zeolites. Zeolites are three dimensional networks built up of $TO_4$ tetrahedra (T=Si or other heteroatom) such that each of the four oxygen atoms is shared with another tetrahedron. The most common forms are aluminosilicates, although structures containing boron, gallium, or iron in place of aluminum and germanium in place of silicon have been reported. See, e.g., L. L. Hegedus, CATALYST DESIGN, PROGRESS AND PERSPECTIVES, p. 165 (Wiley, 1987), which is incorporated by reference herein. Non-zeolitic microporous structures typically contain $AlO_2$ and $PO_2$ oxide units. They can contain silicon and/or one or more metals other than aluminum which will form oxide linkages in tetrahedral coordinates with aluminum and phosphorous in a crystalline network. Common forms are aluminophosphates (AlPO's) and silicoaluminophosphates (SAPO's), the latter with tetrahedrally coordinated $AlO_2$, $PO_2$ and $SiO_2$ units. Other forms in this category include $MO_2$, $AlO_2$ and $PO_2$ tetrahedrally bound structural oxide units, wherein M is selected from the group consisting of arsenic, beryllium, boron, chromium, cobalt, gallium, vanadium, and zinc. See, e.g., U.S. Pat. No. 5,741,759 issued Apr. 21, 1998 to Gee et al., which is incorporated by reference herein.

Preferably, the crystalline microporous catalyst used in the present process is a zeolite posessing a unidimensional pore topology. A preferred zeolite of this type is mordenite. As previously discussed, zeolites typically consist of a microporous network of $SiO_4$ and $AlO_4$ tetrahedra linked together via shared oxygen atoms. Aluminum has a (3+)

valency resulting in an excess negative charge on the $AlO_4$ tetrahedra, which can be compensated by H+ or other cations (Na+, $NH^{4+}$, $Ca^{2+}$). When M is hydrogen the materials are Bronsted acidic, when M is for example Cs the materials are basic. Upon heating, Bronsted acidic hydroxyls condense creating coordinately unsaturated Al, which acts as a Lewis acid site. The acid strength, acid site density and Bronsted versus Lewis acidity are determined by the level of framework aluminium. The ratio of silica/alumina can be varied for a given class of zeolites either by controlled calcination, with or without the presence of steam, optionally followed by extraction of the resulting extra framework aluminium or by chemical treatment employing for example ammonium hexafluorosilicate. It has been found that when a zeolite containing metal sites is used as a catalyst for achieving a high selectivity of branched fatty acid and/or alkyl esters, the catalyst preferably comprises a 10 member ring or a 12 member ring.

The pore topology of the preferred zeolite catalysts herein can impact the efficiency and the shape selectivity of the catalyst. Shape selectivity refers to the size and shape of the molecules that are allowed to enter and leave the pores of the catalyst. Examples of shape selectivity in the present invention include the size and number of branched chains which are isomerized within the parent molecule and the size and concentration of by-products such as substituted aromatics and oligomers which are generated during the course of the reaction. The zeolite catalysts preferred herein typically have the following characteristics: a median pore diameter of from about 4 angstroms to about 9 angstroms, more preferably from about 5 angstroms to about 6 angstroms; and a Langmuir surface area of from about 50 $m^2/g$ to about 900 $m^2/g$, more preferably from about 400 $m^2/g$ to about 750 $m^2$. In order to maximize Bronsted acidity, the $Na_2O$ content of the zeolite is preferably minimized in that the preferred zeolites contain less than about 20% $Na_2O$, preferably less than about 10% $Na_2O$, and more preferably less than about 0.1% $Na_2O$.

The silica/alumina molar ratio ($SiO_2/Al_2O_3$ ratio) of the present zeolite catalysts, which can be determined by atomic absorption photometry, is preferably from about 3 to about 300, and more preferably from about 20 to about 100.

Preferred zeolite catalysts for use herein include pentacyl zeolite (i.e. zeolite ZSM-5), beta zeolite, and/or mordenite. In the present invention, any zeolite can be used, however, the zeolites described above are preferred from the viewpoint of pore size, heat resistance, acid resistance and acid properties. Beta zeolite and pentacyl zeolites are available only as a synthetic substance; while mordenite is available both as a natural substance and as a synthetic substance. The term "pentacyl type zeolite" as used herein, also referred to as ZSM-5 type, is a zeolite composed of oxygen 10-membered ring wherein zigzag pore pathways intersect tunnel-like pore pathways at right angles to form pores. Beta type zeolite is composed of oxygen 12-membered rings, where two of the pore dimensions are elliptical and the third is nearly circular. The mordenite type zeolite, the highest in silicon content among naturally-occurring zeolites, is a zeolite composed of 12-membered rings wherein the pores are formed mainly by tunnel-like pore pathways [Shokubai Koza, Vol. 10, edited by the Catalysis Society of Japan, Kodansha Ltd. (1986)]. Although these zeolites can be synthesized by hydrothermal synthesis [J.C.S., 2158 (1948)], they are also commercially available. For example, commercial products of the pentacyl type include CBV 3024 (having a $SiO_2/Al_2O_3$ ratio of 30), CBV 8014 (having a $SiO_2/Al_2O_3$ ratio of 80), and CBV 28014 (having a $SiO_2/Al_2O_3$ ratio of 280) available from Zeolyst International of Valley Forge, Pa. Commercial products of the mordenite type include CBV 20A (having a $SiO_2/Al_2O_3$ ratio of 20) and CBV 90A (having a $SiO_2/Al_2O_3$ ratio of 90) from Zeolyst International. Commercial beta zeolite products include CP814E (having a $SiO_2/Al_2O_3$ ratio of 25) available from Zeolyst International.

Other suitable classes of zeolites for performing the reaction according to the present invention are the zeolites belonging to the classes of zeolites L and zeolite omega. Zeolites L (including their preparation) have been described in WO 91/06367. Zeolites omega have been described in GB 1,178,186.

It has been found that incorporating metal sites into the zeolite catalyst will effectively isomerize saturated and/or unsaturated fatty acids and/or alkyl esters into branched molecules. While not wishing to be bound by theory, it is believed that the reaction mechanism consists of the following steps. First, any unsaturated fatty acids and/or alkyl esters present are rapidly hydrogenated to their corresponding saturated forms over the metal sites of the catalyst. Second, the saturated fatty acids and/or alkyl esters are randomly dehydrogenated over the metal sites to form low concentrations of unsaturated molecules. Third, the unsaturated fatty acid and/or methyl ester thus formed is skeletally and positionally isomerized over the acid sites of the catalyst. Fourth, the unsaturated, isomerized molecule is rehydrogenated over the metal sites to form the saturated, branched molecule. The preferred zeolite catalysts, previously described, are doped with a metal to form metal sites on the catalyst. Preferably, the zeolite catalyst is doped with a Group VIII metal such as iron, cobalt, nickel, ruthenium, rhodium, palladium, osmium, iridium, and/or platinum. The metal incorporated in the zeolite catalyst is preferably selected from the group consisting of platinum, palladium, nickel, and mixtures thereof. In a more preferred embodiment, the zeolite catalyst is doped with platinum to form platinum sites on the catalyst.

Metal sites are incorporated in the present zeolite catalysts via a number of processes known in the art including incipient wetness impregnation, ion exchange, vapor deposition, and the like. Suitable processes for preparing zeolite catalysts containing metal sites are described in Romero et al., *Ind. Eng. Chem. Res.* 36, 3533–3540 (1997), 37, 3846–3852 (1998); Canizares et al., *Ind. Eng. Chem. Res.* 36, 4797–4808 (1997); Girgis et al., *Ind. Eng. Chem. Res.* 35, 386–396 (1996); which are all hereby incorporated by reference herein. The amount of metal incorporated in the catalyst is typically from about 0.1% to about 10%, by weight of the catalyst. If platinum and/or palladium is incorporated in the catalyst, it is typically at a level of from about 0.1% to about 2%, preferably from about 0.5% to about 1.5%, by weight of the catalyst. If nickel is incorporated in the catalyst, it is typically at a level of from about 1% to about 10%, preferably from about 3% to about 7%, by weight of the catalyst.

The metal sites can be incorporated either on the surface of the catalyst or within the pores of the catalyst, or both. In a preferred embodiment, the metal sites are incorporated within the pores of the zeolite catalyst. It is believed that incorporating the metal within the pores of the zeolite catalyst is more effective in isomerizing saturated fatty acids and/or alkyl esters into branched molecules as opposed to other types of molecules such as alkanes, substituted aromatics, or oligomers. The percent metal dispersion, as measured by CO chemisorption, is typically from about 0.5% to about 100% and preferably at least about 50%.

The isomerization reaction step in the present invention is carried out using the above-described starting material, catalyst containing metal sites, as described hereinbefore. As for specific reaction conditions, it is preferable that the reaction be carried out at a temperature of from about 240° C. to about 380° C., preferably from about 280° C. to about 350° C., and more preferably from about 320° C. to about 340° C. The amount of catalyst, preferably a zeolite catalyst containing metal sites as described hereinbefore, used in the present reaction is typically from about 0.1% to about 20%, preferably from about 0.5% to about 10%, and more preferably from about 1% to about 6%, by weight of the reaction mixture.

The reaction is carried out in the presence of hydrogen gas, or in a mixture of gases including hydrogen gas, such as nitrogen, carbon dioxide, argon, and mixtures thereof. Hydrogen gas is both generated and consumed in the course of the present reaction, and as such is required to be present in the headspace of the reactor. It is preferable to have a net input of hydrogen gas into the present process during the reaction step in order to bring the reaction to completion. Hydrogen is generated during dehydrogenation of the alkyl chain prior to the isomerization step, then consumed during rehydrogenation of the alkyl chain after the isomerization step is completed. Hydrogen is also consumed if there are any significant levels of unsaturated carbon bonds in the starting feedstock, which are hereby converted into saturates in the course of the isomerization reaction.

The present process can further include carrying out the reaction in the presence of a supercritical fluid selected from the group consisting of carbon dioxide, ethene, ethane, propane, and mixtures thereof. The supercritical fluid can speed the overall rate of reaction by greatly increasing the solubility of hydrogen gas into the liquid phase of the reaction.

Also, the reaction is preferably carried out in a closed system, e.g. utilizing an autoclave, where the reaction pressure is normally less than about 1000 pounds per square inch gauge (psig), preferably from about 10 to about 300 psig, and more preferably from about 50 to about 100 psig. Low pressure is recommended is to prevent vaporization of low boiling substances in the system including those substances contained in the catalyst. Higher pressures are less desirable, in that they are associated with more side reactions, e.g. cracking to alkanes.

The process of the present invention typically takes from about 0.1 to about 24 hours, preferably from about 0.5 to about 12 hours, and more preferably from about 1 to about 6 hours. Since the catalyst tends to be poisoned by coke during the reaction, the reaction normally takes from about 1 to about 10 hours. If this problem is overcome, the reaction time can be shortened to several minutes or even several seconds. Also, continuous reaction becomes possible. Excessively long reaction time tends to cause thermal decomposition, resulting in decreased yield.

The reaction apparatus used is preferably an autoclave, because a pressurized reaction system is preferred, but the reaction can also be carried out in a reactor such as a stirred tank or fixed bed reactor. The atmosphere in the apparatus (i.e. headspace) is at least about 1% hydrogen, preferably from about 1% to about 100% hydrogen, more preferably from about 50% to about 100% hydrogen, and still more preferably from about 90% to about 100% hydrogen.

The product obtained by the above-described isomerization reaction contains branched chain saturated fatty acids or esters thereof, when the starting material is a corresponding linear fatty acid or ester, with a high selectivity. The selectivity of branched molecules in the product resulting from the present process is typically from about 1% to about 99%, preferably from about 50% to about 99%, and more preferably from about 75% to about 99%. The branched chain fatty acids, etc. thus obtained normally have alkyl side chains of 1 to 4 carbon atoms. They are normally obtained as a mixture of many isomers with different branching positions. Other components can include alkanes, substituted aromatics, oligomers, and any unreacted linear fatty acid and/or alkyl ester.

The unreacted linear fatty acid and/or alkyl ester in the product mixture can often be converted further into branched molecules by further reaction with catalyst and hydrogen gas. This can be achieved by subjecting the entire product mixture to further reaction, or more preferably, by separating the unreacted linear molecules from the rest of the product mixture and reacting further only this portion of the product stream. This can be efficiently done in a continuous process by recycling the unreacted linear molecules and mixing them with fresh material entering the reaction zone. The reactor preferably converts at least 10% of the linear fatty acid or alkyl ester fed into the reaction zone, more preferably at least 50%.

As mentioned previously, the catalyst tends to be subject to coking, either with unsaturated molecules or with carbon. It is possible to regenerate the catalyst by treatment with an appropriate solvent, such as hexane or octane, followed by drying, calcination, and reduction of the catalyst, the latter being done typically in the presence of hydrogen gas in a muffle furnace.

In order to isolate the branched fatty acid and/or alkyl ester from the rest of the product mixture, a number of separation processes can be performed after the reaction step is complete. Suitable separation processes include, but are not limited to: filtration to recover catalyst, distillation to remove oligomers, solvent or non-solvent based crystallization to remove and recycle the unreacted fatty acid and/or alkyl ester, and/or distillation to remove alkanes and/or aromatics.

All of the documents and references referred to herein are incorporated by reference, unless otherwise specified. All parts, ratios, and percentages herein, in the Specification, Examples, and Claims, are by weight and all numerical limits are used with the normal degree of accuracy afforded by the art, unless otherwise specified.

The following are non-limiting examples of the catalysts and processes of the present invention. The products of the exemplified processes are analyzed using gas chromatography with a flame ionization detector to determine the content of linear chains, branched chains, alkanes, and substituted aromatics in the products of the processes. The calculated selectivity to branched chains of a given process is then calculated based upon the following formula:

$$(\% \text{ of branched chains in product})/(\% \text{ of converted linear chains}) \times 100\%$$

EXAMPLE 1

This example demonstrates the performance of a platinum-doped beta zeolite in the skeletal isomerization of stearic acid.

A platinum doped beta zeolite catalyst is prepared according to the following procedure. About 5.6 grams of zeolite ammonium-beta (Zeolyst, CP 814E) is pre-calcined at 450° C. for 4 hours in a muffle furnace. A solution of 0.075 grams hydrogen hexachloroplatinate (IV) hydrate and 5.425 grams of distilled water is used to impregnate the catalyst. After impregnation, the catalyst is placed in a muffle furnace and dried at 110° C. for 14 hours, calcined again at 450° C. for 5 hours, then reduced at 410° C. for 5 hours in the presence of 500 cc/min of flowing $H_2$ gas. The catalyst, prepared according to the above procedure, has the following properties: surface area of 525 $m^2$/gr, strong acidity of 0.03 meq/gr, Pt metal content of 0.4%, and metal dispersion of 20%.

About 80 grams of stearic acid and 4 grams of Pt/beta zeolite, prepared as described above, are placed in a 300 ml. batch autoclave and mixed for 6 hours at a temperature of 340° C. in the presence of 100 psig hydrogen gas. The product from the reaction is filtered to remove the catalyst, and then distilled at 180° C. and 3 mm Hg pressure to separate the monomer fraction from any higher molecular weight components. The yield of monomer fraction from distillation is 95% and has the following composition:

| linear chain fatty acid | 80.6% |
|---|---|
| branched chains fatty acid | 6% |
| alkanes | 6% |
| substituted aromatics | 7.4% |

The calculated selectivity to branched chain fatty acid (as a percentage of the material converted) is 30%.

The unreacted linear chains are then separated by solvent crystallization. About 50 grams of the monomer fraction from distillation is mixed with 100 grams of hexane and chilled to 15° C. with agitation. The liquid fraction is then filtered from the solid fraction. The yield of the liquid and solid fractions from crystallization are 18.5% and 81.5%, respectively. Both fractions are analyzed by gas chromatography on a solvent free basis for weight % of each component.

| liquid fraction | |
|---|---|
| linear chain fatty acid | 4% |
| branched chain fatty acid | 28% |
| alkanes | 28% |
| substituted aromatics | 40% |
| solid fraction | |
| linear chain fatty acid | 98% |
| branched chain fatty acid | 1% |
| alkanes | 1% |
| substituted aromatics | not detected |

EXAMPLE 2

This example is similar to Example 1 except that stearic methyl ester is used instead of stearic acid. Using the same catalyst, reaction and separation conditions, the composition of the monomer fraction from distillation is as follows:

| linear chain methyl ester | 91.3% |
|---|---|
| branched chain methyl ester | 4.1% |
| alkanes | 1.6% |
| substituted aromatics | 3% |

The calculated selectivity to branched chain methyl ester is 47%.

Solvent crystallization with hexane is performed using the same conditions. The yield of the liquid and solid fractions from crystallization is 7.5% and 92.5%, respectively, on a solvent-free basis. Weight % compositions of each fraction are as follows:

| liquid fraction | |
|---|---|
| linear chain methyl ester | 23% |
| branched chain methyl ester | 27% |
| alkanes | 10% |
| substituted aromatics | 40% |
| solid fraction | |
| linear chain methyl ester | 97% |
| branched chain methyl ester | 2% |
| alkanes | 1% |
| substituted aromatics | not detected |

EXAMPLE 3

This example demonstrates similar performance between a fresh and a regenerated platinum-doped, beta zeolite catalyst.

About 125 grams of stearic acid and 5 grams of Pt/beta zeolite are placed in a 300 ml. batch autoclave and mixed for 6 hours at a temperature of 340° C. in the presence of 100 psig hydrogen gas. The product from the reaction is filtered to remove the catalyst, and has the following composition:

| linear chain fatty acid | 97.7% |
|---|---|
| branched chain fatty acid | 1.1% |
| alkanes | 1.2% |
| substituted aromatics | not detected |

The calculated selectivity to branched chain fatty acid is 48%.

Regeneration is done according to the following procedure. The catalyst is first washed with hexane solvent at 70° C., filtered, and then dried in a muffle furnace at 80° C. for 6 hours. Then it is calcined at 425° C. for 7 hours, and reduced at 425° C. for 7 hours in the presence of 500 cc/min of flowing $H_2$ gas.

The performance of the regenerated catalyst is demonstrated with fresh stearic acid. About 80 grams of stearic acid and 4 grams of regenerated catalyst are reacted using the same conditions as described above. The product from the reaction is filtered to remove the catalyst, and has the following composition:

| linear chain fatty acid | 97% |
|---|---|
| branched chain fatty acid | 1.4% |
| alkanes | 1.6% |
| substituted aromatics | not detected |

The calculated selectivity to branched chain fatty acid is 47%

EXAMPLE 4

This example demonstrates that the product from reaction can be recycled and run to a higher conversion using fresh platinum/beta zeolite catalyst, with consistent reaction selectivity to branched chains.

In the first reaction, 125 grams of stearic acid and 5 grams of Pt/beta zeolite are placed in a 300 ml. batch autoclave and mixed for 6 hours at a temperature of 340° C. in the presence of 100 psig hydrogen gas. The product from the reaction is filtered to remove the catalyst, and has the following composition:

| | |
|---|---|
| linear chain fatty acid | 95% |
| branched chain fatty acid | 3% |
| alkanes | 2% |
| substituted aromatics | not detected |

The calculated selectivity to branched chain fatty acid is 60%.

In the second reaction, 80 grams of the product from the first reaction and 3.65 grams of fresh Pt/Beta zeolite are placed in the autoclave and run under similar conditions to that reported above. The product from the second reaction is filtered, and has the following composition:

| | |
|---|---|
| linear chain fatty acid | 90.7% |
| branched chain fatty acid | 5.4% |
| alkanes | 3.9% |
| substituted aromatics | not detected |

The calculated selectivity to branched chain fatty acid is 58%.

COMPARATIVE EXAMPLE 1

This example shows that both a platinum-doped alumina catalyst and a platinum/chloride doped alumina catalyst have little or no activity for the skeletal isomerization of stearic acid. These catalysts have historically been used in the skeletal isomerization of short chain alkanes such as pentane or hexane (Belloum et al., Revue do L'Institut Francais Du Petrole 46, 92–93, 1991).

The 5% platinum on alumina catalyst is available from Aldrich Chemical Co. (#31,132–4). The platinum/chloride doped alumina catalyst is prepared using the following procedure, as described in detail in U.S. Pat. No. 3.242,228, issued Mar. 22, 1966 to Riordan et al. About 7.5 grams of 1% Pt on alumina catalyst is obtained from Alfa Aesar (#11797). About 1.0 grams of methylene chloride solvent is impregnated onto the catalyst. The catalyst is placed in the muffle furnace and treated at 260° C. for 4 hours.

About 100 grams of stearic acid and 5 grams of platinum/alumina catalyst are placed in a 300 ml. batch autoclave and mixed for 6 hours at a temperature of 340° C. in the presence of 100 psig hydrogen gas. The product from the reaction is filtered to remove the catalyst, and has the following composition:

| | |
|---|---|
| linear chain fatty acid | 98.7% |
| branched chain fatty acid | 0% |
| alkanes: | 1.3% |
| substituted aromatics | not detected |

The calculated selectivity to branched chain fatty acid is 0%.

Likewise, 150 grams of stearic acid and 7.5 grams of platinum/chloride doped alumina catalyst are placed in the autoclave and mixed for 6 hours at a temperature of 320° C. in the presence of 200 psig hydrogen gas. The filtered product has the following composition:

| | |
|---|---|
| linear chain fatty acid | 89.7% |
| branched chain fatty acid | 0.3% |
| alkanes | 10% |
| substituted aromatics | not detected |

The calculated selectivity to branched chain fatty acid is 3%.

COMPARATIVE EXAMPLE 2

This example shows that a non-crystalline, silica-alumina catalyst doped with platinum has little activity for the skeletal isomerization of stearic acid.

An amorphous silica-alumina catalyst (Grace-Davison, 70–90% SiO2 by weight) is impregnated with platinum using the same procedure described in Example 1 above for the Pt/beta zeolite catalyst.

About 85 grams of stearic acid and 5 grams of Pt/silica-alumina catalyst are placed in the autoclave and reacted under the same conditions described in Example 1. The product from the reaction is filtered to remove the catalyst, and has the following composition:

| | |
|---|---|
| linear chain fatty acid | 98.4% |
| branched chain fatty acid | 0.2% |
| alkanes | 1.4% |
| substituted aromatics | not detected |

The calculated selectivity to branched chain fatty acid is 12.5%.

COMPARATIVE EXAMPLE 3

This example shows that a sulfated zirconium oxide catalyst doped with platinum has little activity for the skeletal isomerization of stearic acid. This catalyst has been shown to be effective in isomerization of both short chain (n-heptane) and long chain (n-hexadecane) hydrocarbons (Wen et al., Energy and Fuels, 4, 372–379, 1990).

A platinum-doped, sulfated zirconium oxide catalyst is prepared according to the following procedure. About 9.004 grams of sulfated zirconium hydroxide is obtained from Magnesium Elektron (X20682/01). A solution of 0.119 grams hydrogen hexachloroplatinate (IV) hydrate and 2.898 grams of distilled water are used to impregnate the catalyst. After impregnation, the catalyst is placed in the muffle furnace and dried at 110° C. for 4 hours, calcined at 600° C. for 5 hours, then held at 110° C. for 4 hours. The catalyst, prepared according to the above procedures has the following properties: surface area of 80 m2/gr, pore volume of 0.3 cc/gr, sulfate content of 3.4%, % Pt metal of 0.5%.

About 101 grams of stearic acid and 5.2 grams of platinum doped sulfated zirconium oxide catalyst are placed in a 300 ml. batch autoclave and mixed for 6 hours at a temperature of 320° C. in the presence of 200 psig hydrogen gas. The product from the reaction is filtered to remove the catalyst, and has the following composition:

| | |
|---|---|
| linear chain fatty acid | 97% |
| branched chain fatty acid | 0.5% |
| alkanes | 2.0% |

| -continued | |
|---|---|
| substituted aromatics | 0.5% |

The calculated selectivity to branched chain fatty acid is 17%.

Solvent crystallization with hexane is done using the conditions similar to that of Example 1. The yield of the liquid and solid fractions from crystallization is 6% and 93%, respectively. Weight % compositions of each fraction are as follows:

| liquid fraction | |
|---|---|
| linear chain fatty acid | 46.5% |
| branched chain fatty acid | 8.5% |
| alkanes | 35% |
| substituted aromatics | 10% |
| solid fraction | |
| linear chain fatty acid | 99% |
| branched chain fatty acid | 0% |
| alkanes | 1% |

What is claimed is:

1. A process for branching saturated and/or unsaturated fatty acids and/or alkyl esters thereof comprising the steps of:
   (a) subjecting a feedstock comprising saturated and/or unsaturated fatty acids having from 3 to 25 carbon atoms, alkyl esters thereof, or mixtures thereof, to a skeletal isomerization reaction using a catalyst comprising a crystalline porous structure having incorporated therein a metal to form metal sites on said catalyst; and
   (b) isolating branched fatty acids, alkyl esters thereof, or mixtures thereof, from a reaction mixture obtained by said skeletal isomerization reaction.

2. The process of claim 1 wherein said crystalline porous structure is a crystalline microporous structure.

3. The process of claim 2 wherein said crystalline microporous structure is a zeolite.

4. The process of claim 3 wherein said zeolite is selected from the group consisting of pentacyl zeolite, beta zeolite, mordenite, and mixtures thereof.

5. The process of claim 4 wherein said zeolite has a median pore diameter of from about 4 angstroms to about 9 angstroms.

6. The process of claim 1 wherein said metal to form metal sites is a Group VIII metal.

7. The process of claim 6 wherein said metal sites are located within pores of said crystalline porous structure.

8. The process of claim 6 wherein said Group VIII metal is selected from the group consisting of platinum, nickel, palladium, and mixtures thereof.

9. The process of claim 8 wherein said metal to form metal sites is platinum.

10. The process of claim 1 wherein said skeletal isomerization reaction is carried out in the presence of a hydrogen gas.

11. The process of claim 10 wherein said skeletal isomerization reaction is carried out in the presence of an additional gas selected from the group consisting of nitrogen, carbon dioxide, argon, and mixtures thereof, and wherein a concentration of said hydrogen gas is at least about 1% of the total headspace.

12. The process of claim 10 wherein said skeletal isomerization reaction is further carried out in the presence of a supercritical fluid selected from the group consisting of carbon dioxide, ethene, ethane, propane, and mixtures thereof.

13. The process of claim 10 wherein said skeletal isomerization reaction is carried out at a pressure of less than 1000 pounds per square inch gauge (psig).

14. The process of claim 1 wherein said skeletal isomerization reaction is carried out at a temperature of from about 240° C. to about 380° C.

15. The process of claim 1 wherein said feedstock comprises less than about 50%, by weight of said feedstock, of unsaturated fatty acids, alkyl esters thereof, or mixtures thereof.

16. The process of claim 15 wherein said feedstock comprises saturated fatty acids, alkyl esters thereof, or mixtures thereof and is essentially free of unsaturated fatty acids, alkyl esters thereof, or mixtures thereof.

17. The process of claim 1 wherein a ratio of said saturated and/or unsaturated fatty acids, alkyl esters thereof, or mixtures thereof, to said catalyst is from about 5:1 to about 1000: 1, by weight.

18. The process of claim 1 wherein said process further comprises a recycle step, wherein said recycle step comprises the steps of:
   (a) subjecting said reaction mixture, wherein said reaction mixture is substantially free of branched fatty acids, alkyl esters thereof, or mixtures thereof, to a recycle skeletal isomerization reaction using said catalyst; and
   (b) isolating branched fatty acids, alkyl esters thereof, or mixtures thereof, from a recycle reaction mixture obtained by said recycle skeletal isomerization reaction.

* * * * *